United States Patent [19]
Baba

[11] Patent Number: 5,672,876
[45] Date of Patent: Sep. 30, 1997

[54] METHOD AND APPARATUS FOR MEASURING DISTRIBUTION OF RADIOACTIVE NUCLIDE IN SUBJECT

[75] Inventor: Shigeo Baba, Tokyo, Japan

[73] Assignee: Nemoto & Co., Ltd., Tokyo, Japan

[21] Appl. No.: 464,638

[22] PCT Filed: Oct. 26, 1994

[86] PCT No.: PCT/JP94/01796

§ 371 Date: Jun. 20, 1995

§ 102(e) Date: Jun. 20, 1995

[87] PCT Pub. No.: WO95/12121

PCT Pub. Date: May 4, 1995

[30] Foreign Application Priority Data

Oct. 26, 1993 [JP] Japan .................. 5-266999

[51] Int. Cl.$^6$ ........................... G01T 1/29
[52] U.S. Cl. .......... 250/358.1; 250/308; 250/393
[58] Field of Search ................... 250/303, 308, 250/358.1, 359.1, 393, 363.04

[56] References Cited

U.S. PATENT DOCUMENTS

| | | | |
|---|---|---|---|
| 3,812,360 | 5/1974 | Tkyva | 250/370.01 |
| 4,777,367 | 10/1988 | Kawasaki et al. | 250/358.1 X |
| 5,289,008 | 2/1994 | Jaszczak et al. | 250/363.04 X |

*Primary Examiner*—Edward J. Glick
*Attorney, Agent, or Firm*—Kubovcik & Kubovcik

[57] ABSTRACT

The invention intends to measure true distribution of a radioactive nuclide in respective parts of a subject. A density of each part of a subject sample is measured by measuring the intensity of ionizing radiation for density measurement from a radioactive nuclide for density measurement, which emits the ionizing radiation to each part of the subject sample in the same amount, through the subject sample interposed midway, the intensity of ionizing radiation emitted from another radioactive nuclide existing in each part of the subject sample is measured, and the amount of another radioactive nuclide in each part of the subject sample is determined by compensating the measured intensity of the ionizing radiation from another radioactive nuclide based on the self-absorptivity of each part of the subject sample corresponding to the density thereof.

4 Claims, 4 Drawing Sheets

METHOD AND APPARATUS FOR MEASURING DISTRIBUTION OF RADIOACTIVE NUCLIDE IN SUBJECT

TECHNICAL FIELD

The present invention relates to a method and apparatus for measuring distribution of a radioactive nuclide in a subject by using autoradiography, and more specifically to a measuring method and apparatus to examine distribution of a radioactive nuclide in a subject sample for the purposes of a safety test of drugs or others. In particular, the invention relates to a method and apparatus for measuring distribution of a radioactive nuclide in a subject, which can compensate for differences in density between respective parts of the subject for determining correct distribution of the radioactive nuclide.

BACKGROUND ART

Heretofore, autoradiography has been known as a method for directly recording distribution of a radioactive material in a sample in the form of a photograph.

Specifically, the autoradiography is performed by placing a film closely to, e.g., a sample which contains a radioactive nuclide as a tracer, and exposing the film to ionizing radiation emitted from the sample with a view to determine distribution of the radioactive nuclide deposited in specific parts of the sample.

Such a technique has been especially employed for a safety test of drugs. In a safety test, a drug labeled with a radioactive nuclide is first prepared. The drug is then injected to a laboratory animal such as a rat or a mouse. After a predetermined period of time, the laboratory animal is frozen and sliced to form specimens. After drying the specimens, distribution of the radioactive nuclide in the specimens is measured to thereby determine to which parts of the subject the drug has reached.

In practice, $^{14}C$ of 3 to 5 MBq/weight kg is typically applied as a radioactive nuclide and the laboratory animal is frozen and sliced into specimens each having a thickness of 30 to 90 μm after the predetermined period of time. Here, the maximum range of β-ray radiated from $^{14}C$ is on the order of 25 mg/cm$^2$.

Certainly, to which parts of the subject the injected drug has reached can be determined by employing the above-described technique.

It is also often desired to determine to which parts of the subject the drug has reached in what amounts.

To meet such a demand, in the conventional autoradiography, the amounts of a radioactive nuclide in respective parts of the subject have been measured by exposing each of the frozen and sliced specimens to an X-ray film or an image sensing plate (for RLG, radioluminograpy), and determining an exposure of the film or a PSL value indicating the amount of PSL (photostimulated luminescence) (in the case of radioluminography, RLG).

Meanwhile, in measurement utilizing a photographic action or photostimulated luminescence by radiation, the parameter which comes up in discussion about radioactivity distributed in internal organs is a thickness of the specimen that is expressed by weight per unit area [thickness in terms of (mg/cm$^2$)], i.e., density, rather than by a length (μm).

In this respect, the measuring method using the conventional autoradiography in which only a thickness (μm) of each prepared specimen is indicated suffers from a problem discussed below.

Even if the specimens have the same thickness (μm), internal organs have different densities and water contents from each other and, therefore, radiation is absorbed by the internal organs themselves in different amounts. Consequently, a black tone (of the exposed X-ray film) or a PSL value per unit radioactivity is different for each of the internal organs.

As a result, the black tone of the film or the PSL value is not uniquely in match with the amounts of the radioactive nuclide in different parts of the subject, making it impossible to correctly evaluate distribution of radioactivity in the internal organs of the subject.

To correctly examine distribution of radioactivity in the internal organs of the subject, therefore, to which parts of the subject the drug has reached in how much amounts has been conventionally determined by burning internal organs of a laboratory animal injected with $^{14}C$ in a like manner, and measuring the absolute amount of the radioactive nuclide in each of the internal organs separately. However, that approach has required a very intricate operation.

In view of the above, an object of the present invention is to provide methods of measuring the distribution of radioactivity in respective parts of a subject by autoradiography similar to conventionally used, measuring densities of the respective parts of the subject by using a radioactive nuclide for density measurement, and then measuring true distribution of radioactivity in the respective parts of the subject under examination, keeping in mind that the self-absorptivity of each part of the subject depends on its density.

Yet another object is to provide an apparatus for carrying out the foregoing methods.

DISCLOSURE OF THE INVENTION

The present invention relates to a method of measuring the distribution of a radioactive nuclide in a subject in that a density of each part of a subject sample is measured by measuring the intensity of ionizing radiation for density measurement from a radioactive nuclide for density measurement, which emits the ionizing radiation to each part of the subject sample in the same amount, through the subject sample interposed midway, the intensity of ionizing radiation emitted from another radioactive nuclide existing in each part of the subject sample is measured, and the amount of another radioactive nuclide in each part of the subject sample is determined by compensating the measured intensity of the ionizing radiation from another radioactive nuclide based on the self-absorptivity of each part of the subject sample corresponding to the density thereof.

This invention includes a method for measuring the distribution of a radioactive nuclide in a subject which includes the steps of preparing a data table for density measurement which indicates the relationship between the density of a subject sample and the intensity of β-ray emitted from $^{147}Pm$, as a radioactive nuclide for density measurement, having passed through the subject sample, preparing a data table for compensation of self-absorption which indicates the relationship between the density of the subject sample and the self-absorptivity of the subject sample for radiation from $^{14}C$, as another radioactive nuclide existing in the subject sample, uniformly irradiating ionizing radiation from $^{147}Pm$ to the subject sample which is formed of frozen and sliced specimens and contains $^{14}C$ distributed therein to measure the intensity of the ionizing radiation for density measurement emitted from $^{147}Pm$ and having passed through the subject sample, comparing measured results and data in the data table for density measurement to determine densities of respective parts of the subject sample, measuring distribution of the intensity of ionizing radiation for subject assay emitted from the subject sample which is formed of the frozen and sliced specimens and contains $^{14}C$ distributed therein, and measuring the amounts of $^{14}C$ in the subject sample based on the densities of respective parts of the subject sample, the data table for compensation of self-absorption, and the distribution of the intensity of the ionizing radiation for subject assay.

This invention also provides an apparatus for measuring the distribution of a radioactive nuclide in a subject which includes a density-measurement data table memory storing a data table for density measurement which indicates the relationship between the density of the subject sample and the intensity of β-ray emitted from $^{147}Pm$, as a radioactive nuclide for density measurement, having passed through the subject sample, a self-absorption compensating data table memory storing data table for compensation of self-absorption which indicates the relationship between the density of the subject sample and the self-absorptivity of the subject sample for radiation from $^{14}C$, as a radioactive nuclide for subject assay, density-measurement ionizing radiation reading means for uniformly irradiating ionizing radiation from $^{147}Pm$ to the subject sample which is formed of frozen and sliced specimens and contains $^{14}C$ distributed therein, and for reading the intensity of the density-measurement ionizing radiation emitted from $^{147}Pm$ and having passed through the subject sample, density measuring means for comparing results read by the density-measurement ionizing radiation reading means and data in the density-measurement data table memory to determine densities of respective parts of the subject sample, subject-assay ionizing radiation reading means for reading the intensity of the ionizing radiation emitted from the subject sample which is formed of the frozen and sliced specimens and contains $^{14}C$ distributed therein, self-absorptivity reading means for, based on the density of a certain part of the subject sample determined by the density measuring means, reading a self-absorptivity corresponding to the density of the certain part from the self-absorption compensating data table memory, and ionizing radiation intensity compensating means for compensating the intensity of the ionizing radiation read by the subject-assay ionizing radiation reading means based on the self-absorptivity read by the self-absorptivity reading means.

BEST MODE FOR CARRYING OUT THE INVENTION

One embodiment of the present invention will be described below with reference to an illustrated example.

For carrying out the present invention, a data table for density measurement which indicates the relationship between the density of a subject sample and the intensity of β-ray emitted from $^{147}Pm$, as a radioactive nuclide for density measurement, having passed through the subject sample, and a data table for compensation of self-absorption which indicates the relationship between the density of the subject sample and the self-absorptivity of the subject sample for radiation from $^{14}C$, as a radioactive nuclide for subject assay, are required in advance.

Figure 1:
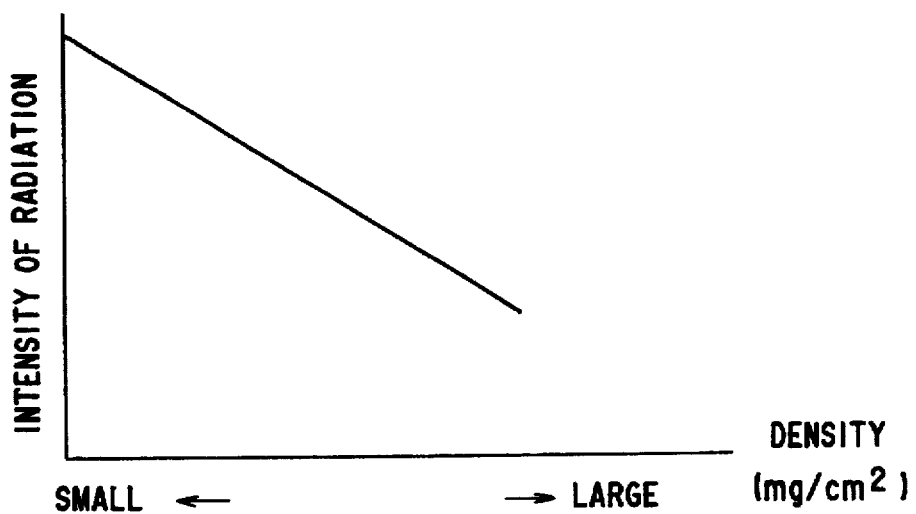
FIG. 1 is a data table for density measurement in which an x-axis represents the density ($mg/cm^2$) and a y-axis represents the radiation intensity arbitrary units.

The data table for density measurement is prepared, as shown in FIG. 1, by plotting the density ($mg/cm^2$) along an x-axis and the radiation intensity in arbitrary units along a y-axis. It will be understood that, by representing the y-axis in logarithmic scale, the relationship of interest is indicated by a substantially straight line declining to the right.

Figure 2:
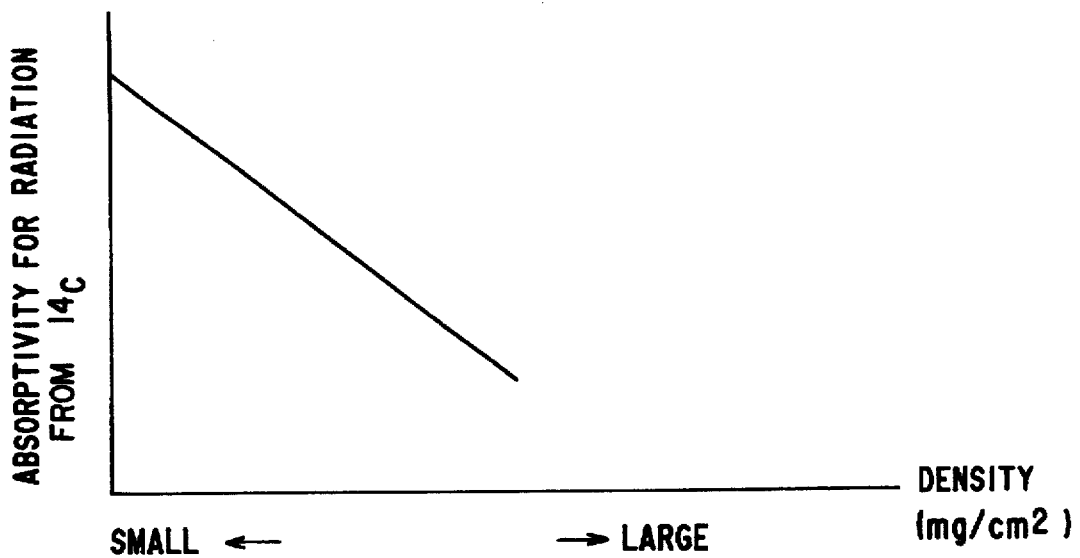
FIG. 2 is a data table for compensation of self-absorption in which an x-axis represents the density ($mg/cm^2$) and a y-axis represents the absorptivity for radiation from $^{14}C$.

On the other hand, the data table for compensation of self-absorption is prepared, as shown in FIG. 2, by plotting the density ($mg/cm^2$) along an x-axis and the absorptivity for the radiation from $^{14}C$ along a y-axis. It will be understood that, by representing the y-axis in logarithmic scale, the relationship of interest is indicated by a substantially straight line declining to the right.

Actual measurement is then performed.

A subject sample is first prepared by freezing and slicing respective parts of a subject over its entire body, which has been injected with $^{14}C$ beforehand, into specimens each having a thickness of 30 μm after a predetermined period of time from the injection.

It is here assumed that the density ($mg/cm^2$) of internal organs in the form of specimens ranges from 0.3 $mg/cm^2$ given by the specimen in which most part is moisture and a solid is on the order of 10 w/v % when dried, to 3.0 $mg/cm^2$ given by the specimen such as sliced from a bony portion in which a solid is 100 w/v %.

For convenience of measurement, the specimens are pasted to a tape with a density of 10 $mg/cm^2$ and a thin film (0.5 $mg/cm^2$) such as a lamellar film is further covered thereon.

Accordingly, the density of an object to be measured, including the tape, ranges from 10.8 $mg/cm^2$ to 13.5 $mg/cm^2$.

Thereafter, all the specimens are arranged adjacent to a slit while the spacing between a source as a radioactive nuclide for density measurement, from which ionizing radiation for density measurement is irradiated, and the slit is set to 10 mm.

In order that the resolution of a density image takes 1.0 mm, the slit of a radiation detector must be set to have a size of 0.5 (in the scan direction)×50.0 mm (corresponding to the width of a rat sample). The area of the thus-sized slit occupies $4 \times 10^{-4}$ (=geometrical efficiency) of the total surface area of a sphere whose radius is 10 mm. $^{147}Pm$ of 3.7 GBq is here used as the radioactive nuclide for density measurement.

It is further assumed to ignore absorption of the radiation by the air residing between the radioactive nuclide for density measurement and the radiation detector.

Subsequently, when the specimens making up the subject sample are scanned at a speed of 10 mm/min, some point on the specimens can be thought as existing in the slit of the aforementioned size for three seconds.

On that condition, the number of β-particles entering the slit is given by:

$$3.7 \times 10^9 \times 4 \times 10^{-4} \times 3 = 4.4 \times 10^6$$

Taking into account the presence of a scattering layer between the radioactive nuclide for density measurement and the radiation detector, the number of β-particles entering the radiation detector is about $4 \times 10^5$.

Figure 3:
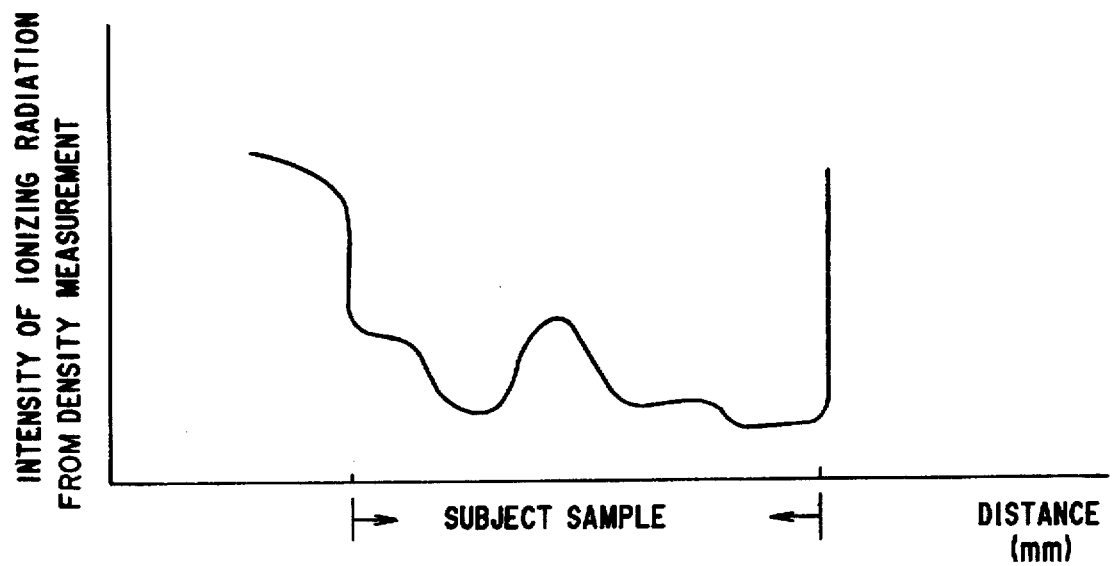
FIG. 3 is a graph showing the result of density measurement for a subject sample in which an x-axis represents the distance in the direction of length of the subject sample and a y-axis represents the intensity of ionizing radiation emitted from a radioactive nuclide for density measurement and detected through the subject sample interposed midway.

FIG. 3 shows one example of results of measuring the subject sample in such a way. In FIG. 3, an x-axis represents the distance in the direction of length of the subject sample and a y-axis represents the result of measuring the intensity of ionizing radiation for density measurement emitted from the radioactive nuclide for density measurement through the subject sample.

If the subject sample has a uniform density in its all parts, the y-axial value thus measured and plotted in FIG. 3 would be constant. Variations in the y-axial value mean that the respective parts of the subject sample have different densities from each other. The density of the subject sample varying in the x-axial direction can be determined by combining the measured value shown in FIG. 3 and the data table for density measurement, shown in FIG. 1, prepared in advance.

Figure 4:
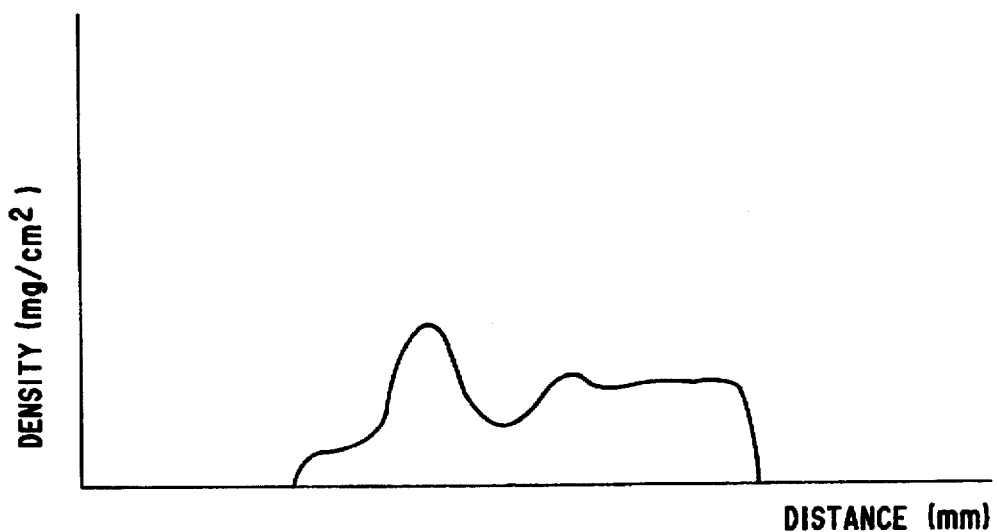
FIG. 4 is a graph in which an x-axis represents the distance in the direction of length of the subject sample and a y-axis represents the density.

The density of the subject sample determined in such a way is shown in FIG. 4. In FIG. 4, an x-axis represents the distance in the direction of length of the subject sample and a y-axis represents the density.

After or before the above step, the intensity of ionizing radiation emitted from $^{14}C$ distributed in the subject sample is measured. The resulting value represents a measured value of the intensity of ionizing radiation emitted from the radioactive nuclide for subject assay residing in the subject sample and left after self-absorption by the subject sample.

Figure 5:
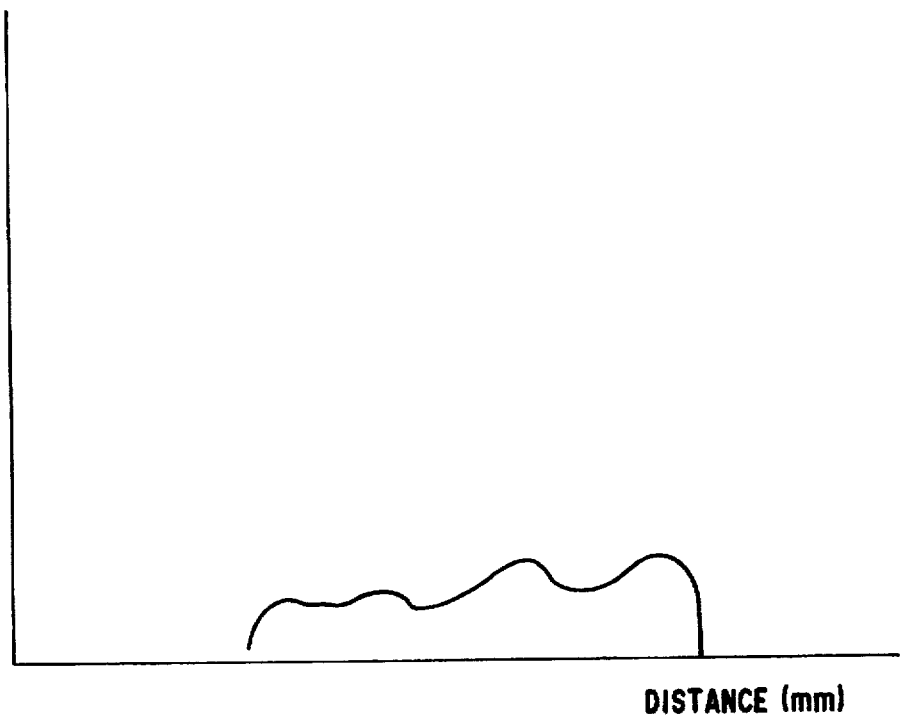
FIG. 5 is a graph in which an x-axis represents the distance in the direction of length of the subject sample and a y-axis represents the apparent intensity of ionizing radiation emitted from $^{14}C$ distributed in the subject sample.

FIG. 5 shows the result of measuring the intensity of the ionizing radiation in such a way. In FIG. 5, an x-axis represents the distance in the direction of length of the subject sample and a y-axis represents the apparent intensity of the ionizing radiation emitted from $^{14}C$ distributed in the subject sample.

Some of the ionizing radiation emitted from the radioactive nuclide for subject assay residing in the subject sample is self-absorbed by the subject sample. The amount of self-absorbed ionizing radiation depends on the density of the subject sample, and the relationship therebetween is shown in FIG. 2.

Therefore, when some part of the subject sample takes a self-absorptivity of 0.5 corresponding to the density measured at the same part, the true amount of the radioactive nuclide for subject assay distributed in that part of the subject sample can be determined by doubling the y-axial value shown in FIG. 5 for that part.

Figure 6:
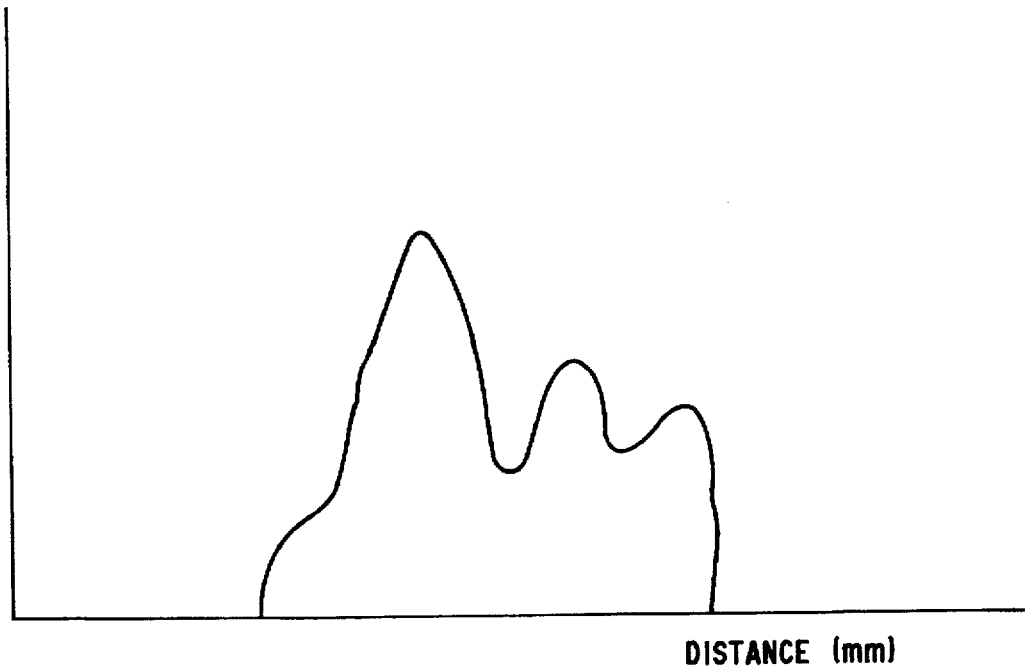
FIG. 6 is a graph in which an x-axis represents the distance in the direction of length of the subject sample and a y-axis represents the amount of a radioactive nuclide for subject assay distributed in the subject sample.

FIG. 6 shows the true amount of the radioactive nuclide for subject assay determined in such a way. In FIG. 6, an x-axis represents the distance in the direction of length of the subject sample and a y-axis represents the amount of the radioactive nuclide for subject assay distributed in the subject sample.

With the measuring method described above, the amount of the radioactive nuclide for subject assay actually distributed in the subject sample can be measured with no need of any intricate operation such as burning the subject.

In the foregoing description, the intensity of ionizing radiation can be measured based on, e.g., the black tone (of an X-ray film) or the PSL value (by radioluminography, RLG) per unit radioactivity.

While the foregoing description has been made as visually reading the measured values and comparing them, arithmetic operations including the comparison may be executed by using a computer.

Figure 7:
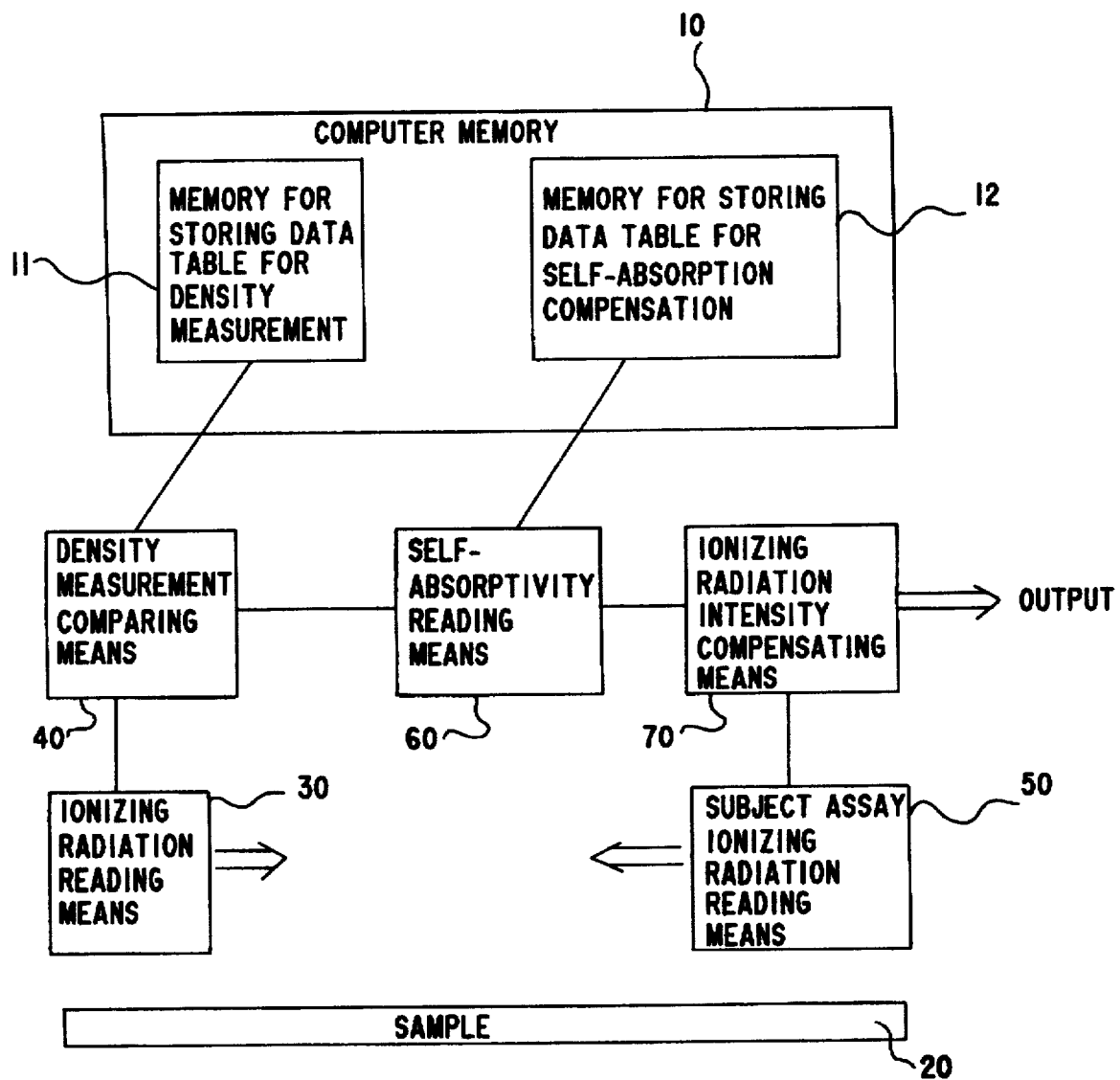
FIG. 7 is a block diagram of a measuring apparatus.

In this case, as schematically shown in FIG. 7, a memory 10 of a computer is configured to set up a memory 11 storing the data table for density measurement which indicates the relationship between the density of the subject sample and the intensity of β-ray emitted from $^{147}Pm$, as the radioactive nuclide for density measurement, having passed through the subject sample, and a memory 12 storing the data table for compensation of self-absorption which indicates the relationship between the density of the subject sample and the self-absorptivity of the subject sample for the radiation from $^{14}C$, as the radioactive nuclide for subject assay.

The computer is combined with a density-measurement ionizing radiation reading means 30 for uniformly irradiating ionizing radiation from $^{147}Pm$ to a subject sample 20 which is formed of frozen and sliced specimens and contains $^{14}C$ distributed therein, and for reading the intensity of the density-measurement ionizing radiation emitted from $^{147}Pm$ and having passed through the subject sample 20, a density measuring means 40 for comparing results read by the density-measurement ionizing radiation reading means 30 and data in the data table memory 11 for density measurement to determine densities of respective parts of the subject sample 20, a subject-assay ionizing radiation reading means 50 for reading the intensity of the ionizing radiation emitted from the subject sample 20 which is formed of the frozen and sliced specimens and contains $^{14}C$ distributed therein, a self-absorptivity reading means 60 for, based on the density of a certain part of the subject sample 20 determined by the density measuring means 40, reading a self-absorptivity corresponding to the density of the certain part from the data table memory 12 for compensation of self-absorption, and an ionizing radiation intensity compensating means 70 for compensating the intensity of the ionizing radiation read by the subject-assay ionizing radiation reading means 50 based on the self-absorptivity read by the self-absorptivity reading means 60. With such an arrangement, the true amounts of the radioactive nuclide for subject assay distributed in the respective parts of the subject sample 20 can be measured.

Additionally, it is possible in the above case to employ, as the density-measurement ionizing radiation reading means 30 or the subject-assay ionizing radiation reading means 50, a reader for linearly or two-dimensionally reading the intensity of ionizing radiation while scanning the subject sample.

In the case of using a reader for two-dimensionally reading the intensity of ionizing radiation, the reading is performed by dividing the scanned area into dots in the form of 0.1 mm square, for example, and executing image processing on those dots.

The foregoing description has been made as continuously measuring the entire subject sample 20 at a time.

It is, however, usually desired to measure only the amounts of $^{14}C$ in the respective internal organs.

Therefore, results of measuring the amounts of $^{14}C$ in the respective internal organs will be described below in the order of successive steps. Note that experiments were conducted by preparing one specimen being 30 μm thick, three specimens being 60 μm thick, and one specimen being 90 μm thick for each of the internal organs.

First, Table 1 lists the results of measuring densities of the respective internal organs.

TABLE 1

|  | 30 μm |  | 60 μm |  | Average | 90 μm |
|---|---|---|---|---|---|---|
| lung | 0.42 | 1.16 | 1.08 | 1.23 | 1.15 ± 0.08 | 1.56 |
| liver | 0.89 | 1.67 | 1.73 | 1.97 | 1.79 ± 0.16 | 2.60 |
| heart | 0.63 | 1.25 | 1.28 | 1.32 | 1.28 ± 0.16 | 1.88 |
| testis | 0.20 | 0.59 | 0.72 | 0.95 | 0.75 ± 0.18 | 1.19 |
| kidney | 0.63 | 1.25 | 1.37 | 1.59 | 1.40 ± 0.17 | 2.31 |
| muscle | 0.30 | 1.20 | 1.40 | 1.58 | 1.39 ± 0.19 | 1.65 |
| brain | 0.57 | 0.89 | 0.98 | 1.29 | 1.04 ± 0.19 | 1.92 |
| adrenal | 0.86 | 1.47 | 1.73 | 1.77 | 1.66 ± 0.16 | 2.25 |
| thymus | 0.59 | 1.20 | 1.23 | 1.32 | 1.25 ± 0.06 | 1.86 |

These measured results correspond to the graph of FIG. 4 in the embodiment described above. Accordingly, the results of Table 1 can be derived by preparing the data table for density measurement as shown in FIG. 1 and obtaining the results of measuring the intensity of the density-measurement ionizing radiation emitted from $^{147}$Pm, as the radioactive nuclide for density measurement, through the subject sample interposed midway prior to the step of making the list of Table 1.

As will be seen from Table 1, comparing the data on the specimens being 60 μm thick, the density of the liver is about 2.4 times that of the testis. It will be also understood that the muscle and the kidney have substantially the same density. However, the data for each of the internal organs is varied with no proportional relation between the specimen being 30 μm thick, the specimens being 60 μm thick, and the specimen being 90 μm thick.

Next, the apparent intensity of the ionizing radiation emitted from $^{14}$C distributed in the respective internal organs of the subject was measured. Table 2 lists the measured results.

TABLE 2

|  | 30 μm |  | 60 μm |  | Average | 90 μm |
|---|---|---|---|---|---|---|
| lung | 81.5 | 150.6 | 148.6 | 149.4 | 149.5 ± 1.0 | 194.1 |
| liver | 40.2 | 73.6 | 70.7 | 76.5 | 73.6 ± 2.9 | 91.8 |
| heart | 91.6 | 166.3 | 163.1 | 167.9 | 165.8 ± 2.4 | 209.9 |
| testis | 9.7 | 19.5 | 19.5 | 20.1 | 19.7 ± 0.3 | 27.5 |
| kidney | 152.4 | 252.4 | 263.6 | 264.8 | 260.3 ± 6.8 | 289.4 |
| muscle | 15.0 | 28.3 | 28.6 | 29.7 | 28.9 ± 0.7 | 33.7 |
| brain | 2.9 | 6.1 | 6.0 | 5.4 | 5.8 ± 0.4 | 8.5 |
| adrenal | 39.7 | 68.8 | 70.0 | 76.3 | 71.7 ± 4.0 | 80.5 |
| thymus | 14.9 | 31.6 | 29.4 | 33.4 | 31.5 ± 1.6 | 47.3 |

These measured results correspond to the graph of FIG. 5 in the embodiment described above.

As will be seen from Table 2, the intensity of the ionizing radiation from the liver is about 3.7 times that from the testis. It will be also understood that the intensity of the ionizing radiation from the kidney is about 9.0 times that from the muscle. However, the data for each of the internal organs is varied with no proportional relation between the specimen being 30 μm thick, the specimens being 60 μm thick, and the specimen being 90 μm thick.

Next, the amounts of the radioactive nuclide for subject assay distributed in the respective internal organs of the subject were measured. Table 3 lists the measured results.

TABLE 3

|  | 30 μm |  | 60 μm |  | Average | 90 μm |
|---|---|---|---|---|---|---|
| lung | 0.231 | 0.464 | 0.455 | 0.466 | 0.462 ± 0.006 | 0.631 |
| liver | 0.120 | 0.242 | 0.234 | 0.262 | 0.262 ± 0.014 | 0.342 |
| heart | 0.266 | 0.520 | 0.511 | 0.529 | 0.520 ± 0.009 | 0.710 |
| testis | 0.027 | 0.056 | 0.057 | 0.061 | 0.058 ± 0.003 | 0.085 |
| kidney | 0.443 | 0.789 | 0.836 | 0.862 | 0.829 ± 0.037 | 1.036 |
| muscle | 0.042 | 0.088 | 0.091 | 0.097 | 0.092 ± 0.005 | 0.111 |
| brain | 0.008 | 0.018 | 0.018 | 0.017 | 0.018 ± 0.001 | 0.029 |
| adrenal | 0.118 | 0.232 | 0.232 | 0.254 | 0.239 ± 0.013 | 0.286 |
| thymus | 0.043 | 0.092 | 0.092 | 0.105 | 0.096 ± 0.008 | 0.159 |

These measured results correspond to the graph of FIG. 6 in the embodiment described above. Accordingly, the results of Table 3 can be derived by obtaining the densities of the respective internal organs listed in Table 1 and the apparent intensities of the ionizing radiation emitted from $^{14}$C distributed in the respective internal organs of the subject listed in Table 2 prior to the step of making the list of Table 3.

As will be seen from Table 3, the amount of the radioactive nuclide for subject assay in the liver is about 4.2 times that in the testis. It will be also understood that the amount of the radioactive nuclide for subject assay in the kidney is about 9.0 times that in the muscle. Further, comparing the data listed in Table 3 relating to the specimen being 30 μm thick, the specimens being 60 μm thick, and the specimen being 90 μm thick, the amount of $^{14}$C distributed in each internal organ of the subject is increased proportionally to the thickness of the specimen. From this, it has been confirmed that the amount of $^{14}$C distributed in each internal organ is correctly measured irrespective of the thickness of the specimen.

Stated otherwise, it will be seen that, taking the subject sample formed of the specimens being 60 μm thick as an example, the ratio of the apparent intensity of the ionizing radiation emitted from $^{14}$C distributed in the testis to that in the liver is 1:3.7, but the ratio of the amount of the radioactive nuclide for subject assay in the testis to that in the liver is 1:4.2 since the density ratio between the two organs is 1:2.4.

Similarly, it will also be seen that, taking the subject sample formed of the specimens being 60 μm thick as an example, the ratio of the apparent intensity of the ionizing radiation emitted from $^{14}$C distributed in the muscle to that in the kidney is 1:9.0, and the ratio of the amount of the radioactive nuclide for subject assay in the muscle to that in the kidney is substantially equal to the above ratio in the apparent intensity of the ionizing radiation emitted from $^{14}$C between the two organs, i.e., 1:9.0, since both the organs have substantially the same density.

From those results, it can be understood that the amount of the radioactive nuclide for subject assay in each of the internal organs is affected by its density and is not directly represented by the apparent intensity of the ionizing radiation emitted from $^{14}$C distributed therein.

INDUSTRIAL APPLICABILITY

As described above, the method and apparatus for measuring distribution of a radioactive nuclide in a subject according to the present invention is especially suitable to compensate for differences in density between respective parts of the subject and to determine a correct distribution of the radioactive nuclide, when examining distribution of the radioactive nuclide in the subject for the purposes of a safety test of drugs or others.

What is claimed is:

1. A method of measuring a distribution of a radioactive nuclide in a subject, comprising determining a density of each part of a subject sample by measuring the intensity of ionizing radiation which passes through said subject sample after being emitted from a first radioactive nuclide of $^{147}$Pm, such that said first radioactive nuclide emits ionizing radiation to each part of said subject sample in the same amount, measuring the intensity of ionizing radiation emitted from a second radioactive nuclide $^{14}$C present in each part of said subject sample, and determining an amount of said second radioactive nuclide in said each part by compensating the measured intensity of the ionizing radiation from said second radioactive nuclide based on a self-absorptivity of said each part corresponding to the density thereof.

2. A method of measuring a distribution of a radioactive nuclide in a subject, comprising preparing a data table for density measurement which indicates a relationship between the density of a subject sample and an intensity of β-ray radiation emitted from $^{147}$Pm and having passed through said subject sample, preparing a data table for compensation of self-absorption which indicates a relationship between the density of said subject sample and a self-absorptivity of said subject sample for radiation from $^{14}$C as a second nuclide present in said subject sample, uniformly irradiating said subject sample with ionizing β-ray radiation from $^{147}$Pm, said subject sample containing $^{14}$C distributed therein, and measuring the intensity of the ionizing radiation from $^{147}$Pm having passed through said subject sample for density measurement, comparing measured results and data in said data table for density measurement to determine densities of respective parts of said subject sample, measuring a distribution of the intensity of ionizing radiation for a subject assay emitted from $^{14}$C in said subject sample, and measuring the amounts of $^{14}$C in said subject sample based on the densities of respective parts of said subject sample, said data table for compensation of self-absorption, and the distribution of the intensity of said ionizing radiation for subject assay.

3. The method of claim 2, wherein said subject sample comprises a frozen specimen having a thickness of 30 to 90 microns.

4. An apparatus for measuring a distribution of a radioactive nuclide in a subject, comprising a density-measurement data table memory storing a data table for density measurement which indicates a relationship between a density of a subject sample and an intensity of β-ray emitted from $^{147}$Pm and having passed through said subject sample, a self-absorption compensating data table memory storing a data table for compensation of self-absorption which indicates a relationship between the density of said subject sample and a self-absorptivity of said subject sample for radiation from $^{14}$C, density-measurement ionizing radiation reading means for uniformly irradiating ionizing radiation from $^{147}$Pm upon said subject sample which contains $^{14}$C distributed therein, and for reading the intensity of the ionizing radiation emitted from $^{147}$Pm after it has passed through said subject sample, density measuring means for comparing results read by said density-measurement ionizing radiation reading means and data in said density-measurement data table memory to determine densities of respective parts of said subject sample, subject-assay ionizing radiation reading means for reading a distribution of the intensity of ionizing radiation emitted from $^{14}$C said subject sample, self-absorptivity reading means for, based on the density of a certain part of said subject sample determined by said density measuring means, reading a self-absorptivity corresponding to the density of said certain part from said self-absorption compensating data table memory, and ionizing radiation intensity compensating means for compensating the distribution of the intensity of the ionizing radiation read by said subject-assay ionizing radiation reading means based on the self-absorptivity read by said self-absorptivity reading means.

* * * * *